(12) United States Patent
Guetta

(10) Patent No.: US 7,286,697 B2
(45) Date of Patent: Oct. 23, 2007

(54) SYSTEM FOR IMAGING AN EXTENDED AREA

(75) Inventor: Avishay Guetta, Rehovot (IL)

(73) Assignee: Applied Materials, Israel, Ltd., Rehovot (IL)

( * ) Notice: Subject to any disclaimer, the term of this patent is extended or adjusted under 35 U.S.C. 154(b) by 743 days.

(21) Appl. No.: 10/274,751

(22) Filed: Oct. 18, 2002

(65) Prior Publication Data

US 2004/0076322 A1    Apr. 22, 2004

(51) Int. Cl.
    *G06K 9/00* (2006.01)
(52) U.S. Cl. ..................................... 382/145
(58) Field of Classification Search ............... 382/145
    See application file for complete search history.

(56) References Cited

U.S. PATENT DOCUMENTS

| | | | |
|---|---|---|---|
| 5,179,419 A * | 1/1993 | Palmquist et al. | 356/73.1 |
| 5,371,690 A * | 12/1994 | Engel et al. | 382/151 |
| 5,828,770 A * | 10/1998 | Leis et al. | 382/103 |
| 5,982,915 A * | 11/1999 | Doi et al. | 382/130 |
| 6,366,690 B1 * | 4/2002 | Smilansky et al. | 382/149 |
| 6,768,543 B1 * | 7/2004 | Aiyer | 356/237.4 |
| 6,816,249 B2 * | 11/2004 | Fairley et al. | 356/237.1 |
| 6,956,963 B2 * | 10/2005 | Ulrich et al. | 382/154 |
| 2001/0048521 A1 * | 12/2001 | Vaez-Iravani | 356/237.2 |
| 2003/0016882 A1 * | 1/2003 | Riley et al. | 382/275 |
| 2005/0249395 A1 * | 11/2005 | Miller | 382/145 |

\* cited by examiner

*Primary Examiner*—Bhavesh M Mehta
*Assistant Examiner*—Jonathan Schaffer
(74) *Attorney, Agent, or Firm*—Tarek N. Fahmi

(57) ABSTRACT

A method for optical inspection and an apparatus for optical inspection of a surface of a substrate, the apparatus includes (i) An optical head comprising a two-dimensional matrix of photodetectors, which is positioned opposite the substrate so as to capture a sequence of area images of respective areas of the surface, (ii) A rotation device, which is coupled to rotate the substrate about a rotation axis, (iii) A translation device, coupled to impart motion to at least one of the optical head and the rotation device so that the optical head is translated radially relative to the substrate while the rotation device rotates the substrate, whereby the area images in the sequence are arrayed in a spiral pattern with respect to the surface, and (iv) An image processor, which is coupled to receive and process the area images so as to determine a characteristic of the surface.

20 Claims, 1 Drawing Sheet

SYSTEM FOR IMAGING AN EXTENDED AREA

FIELD OF THE INVENTION

The present invention relates generally to systems and methods for optical inspection, and specifically to systems for detecting and classifying defects on substrates such as semiconductor wafers.

BACKGROUND OF THE INVENTION

Optical inspection is commonly used in semiconductor device manufacturing to detect defects on the surface of a wafer, such as contaminant particles, scratches and digs. Undetected defects can cause device failures, thus reducing substantially the process yield. Therefore, careful inspection is required to verify the cleanliness and quality both of unpatterned wafers and of patterned wafers at various stages in the manufacturing process.

A common method for inspecting semiconductor wafers is to scan a laser beam over the wafer surface, and measure the light scattered from each point on which the beam is incident. One such method, based on dark-field scattering detection, is proposed by Smilansky et al., in U.S. Pat. No. 6,366,690, whose disclosure is incorporated herein by reference. Smilansky et al. describe a wafer inspection system based on an optical detection head that comprises a laser and a number of light sensors, which are fed by fiberoptic light collectors arrayed around the laser. The optical head is positioned over the wafer surface, and the wafer is rotated and translated so that the laser beam scans over the surface. The sensors detect the radiation that is scattered from the surface in different angular directions simultaneously, as determined by the positions of the fiberoptics. The entire wafer surface is thus scanned, one pixel at a time, along a spiral path.

Another dark-field wafer inspection system is described by Marxer et al., in U.S. Pat. No. 6,271,916, whose disclosure is incorporated herein by reference. In this system, a laser beam is directed toward the wafer surface in a normal direction and scans the surface along a spiral path. An ellipsoidal mirror is used to collect the laser radiation that is scattered from the surface at angles away from the normal. Preferably, light scattered within a first range of angles is collected by one detector, while that scattered within a second range of angles is scattered by another detector. The different detector signals are used to distinguish large defects from small defects.

SUMMARY OF THE INVENTION

It is an object of some aspects of the present invention to provide systems and methods for imaging a substrate at high-speed, and particularly for image-based inspection of semiconductor wafers.

Spiral scanning patterns have been found to be advantageous for high-speed wafer inspection, because they can be implemented simply and compactly, without the use of moving parts in the optical system. The spiral scan is better-suited for covering the surface of a circular wafer than a conventional X-Y rectilinear scan, and such a scan can easily be adjusted for a larger or smaller inspection area. Spiral scan systems known in the art, however, such as those described in the Background of the Invention, are limited to scanning the wafer surface one pixel at a time, along a single, very long spiral scan path.

Preferred embodiments of the present invention provide a system for capturing high-resolution images of a substrate, based on spiral scanning of an optical imaging head over the surface of the substrate, such as a semiconductor wafer. The head includes a light source, preferably a pulsed, incoherent light source, which illuminates a succession of small areas along a spiral scan path over the surface. An image sensor, typically comprising a two-dimensional matrix of photodetectors, captures an image of each of the areas illuminated by the light source. The scan path, scanning speed and pulse rate of the light source are preferably chosen so that the area images captured by the image sensor cover substantially the entire surface of the substrate.

An image processor receives the area images captured by the image sensor and processes them to detect defects on the surface. Optionally, the image processor stitches the area images together to create a combined image of the entire surface. The image processor preferably performs image enhancement operations, as well, such as sharpening and removing noise from the image. These operations most preferably include two-dimensional neighborhood operations, in which each pixel in an area image is processed together with pixels adjoining it in both the vertical and horizontal directions. Operations of this sort cannot be readily performed in spiral scanning systems known in the art, since each pixel along the scan path has neighbors only along the scan path, and not transverse to it.

The present invention will be more fully understood from the following detailed description of the preferred embodiments thereof, taken together with the drawings in which:

DETAILED DESCRIPTION OF PREFERRED EMBODIMENTS

Figure 1:
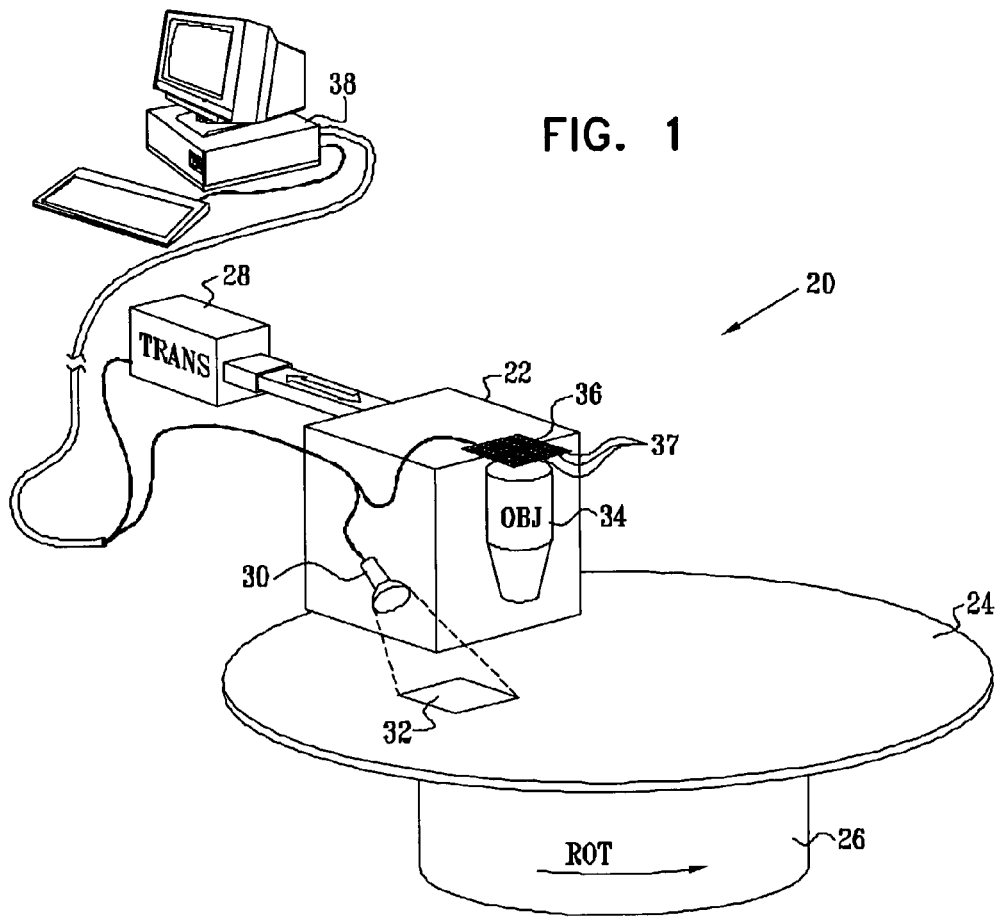
FIG. 1 is a schematic, pictorial illustration of an optical inspection system, in accordance with a preferred embodiment of the present invention.

FIG. 1 is a schematic, pictorial illustration of a system 20 for optical inspection of a semiconductor wafer 24, in accordance with a preferred embodiment of the present invention. The wafer may be either unpatterned or patterned, in substantially any stage of its manufacturing process. An optical head 22, scanning on a spiral path, is used to capture a sequence of area images of the wafer surface, as described in detail hereinbelow.

Wafer 24 is preferably held by a rotating chuck 26, as is known in the art, or by another suitable rotation device. A translation device 28 translates optical head 22 over the wafer surface in a direction perpendicular to the rotation axis of the chuck. The rotation of wafer 24 and translation of head 22 are such as to enable the optical head to scan the entire wafer surface in a spiral pattern. Alternatively, the translational motion may be applied to the wafer, rather than to the optical head. Rotational motion may also be applied to the optical head. Suitable mechanical arrangements for scanning a spiral pattern over a semiconductor wafer are described in detail both by Smilansky et al. and by Marxer et al. in the above-cited patents.

Optical head 22 comprises a light source 30, which illuminates an area 32 on the surface of wafer 24, preferably in a dark-field configuration as shown in the figure. For uniform lighting of area 32, head 22 may comprise multiple light sources or a ring light source positioned around area 32. An objective lens 34 collects light scattered from area 32 and images the light onto an image sensor 36. The image sensor comprises a two-dimensional matrix array of photodetector elements 37. Typically, sensor 36 comprises a CCD or CMOS image sensor, as are known in the art. Sensor 36 forms an area image of area 32 comprising a matrix of pixels, corresponding to elements 37 of sensor 36. Optionally, optical head 22 also includes a rotating filter (not shown), whose rotation is keyed to the rotation of chuck 26, in order to enhance or suppress certain image features on wafer 24. The design and operation of such a filter are described in co-pending U.S. patent application Ser. No. 10/208,113 filed Jul. 29, 2002, titled "Process and assembly for non-destructive surface inspection", which is assigned to the assignee of the present patent application and whose disclosure is incorporated herein by reference.

Image sensor 36 captures the sequence of area images of the wafer surface while chuck 26 and rotation device 28 rotate an translate the wafer is rotating. Therefore, to ensure that the images are not blurred by motion, light source 30 is preferably pulsed. Most preferably, the light source comprises a non-coherent pulsed source, such as a flashlamp with suitable focusing optics, such as a mirror and/or condenser lens. A laser source may alternatively be used, but is generally not necessary since area 32 is relatively large. The illumination produced by the light source may comprise either narrowband light or broadband, white light, depending on whether sensor 36 is to form monochrome or color images. If light source 30 is sufficiently powerful, it can illuminate the entire wafer surface with each of its pulses, in which case the light source may be mounted separately from the optical head.

The area images captured by optical head 32 are received by an image processor 38, which typically processes the area images to detect defects on the surface of wafer 24. Optionally, the image processor combines the area images into a composite image of the entire surface of the wafer. Alternatively, only a portion of the wafer surface may be imaged if desired. Processor 38 typically comprises a general-purpose computer with suitable image processing software for creating the composite image. In addition, processor 38 may comprise a digital signal processor (DSP) or dedicated hardware logic circuits for carrying out computation-intensive image processing steps, such as digital filtering and image rotation, which may be used in analyzing, enhancing and combining the area images.

Figure 2:
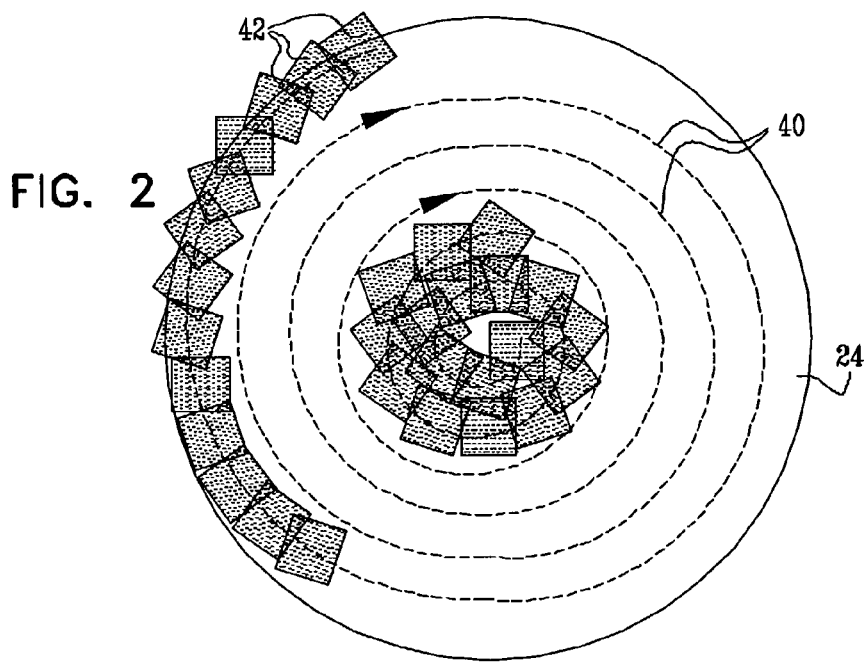
FIG. 2 is a schematic top view of a wafer inspected using the inspection system of FIG. 1, illustrating a pattern of area images of the wafer surface that are captured by the system, in accordance with a preferred embodiment of the present invention.

FIG. 2 is a schematic top view of wafer 24, showing a spiral pattern 40 of area images 42 of the wafer captured by optical head 22, in accordance with a preferred embodiment of the present invention. The spiral pattern of the area images corresponds to the spiral scan of optical head 22 over wafer 24, due to the simultaneous operation of chuck 26 and translation device 28. Each of area images 42 preferably overlaps its neighbors, so that the area images cover substantially the entire wafer surface. It is desirable, however, to reduce the amount of overlap to the minimum necessary to ensure coverage of the entire wafer, in order to reduce the amount of data that processor 38 must handle. For this purpose, either the speeds of chuck 26 and translation device 28 may be varied, or the rate at which sensor 36 captures images may change as a function of position, or both.

The requirements of optical head 22 may be estimated based on the pattern of area images shown in FIG. 2. Assuming that wafer 24 is 30 cm in diameter, and that the wafer surface is to be imaged with spatial resolution of 2 µm, the number of pixels in the composite image of the entire surface will be about $1.8 \times 10^{10}$. If sensor 36 is made up of 4 million detector elements 37 (for example, a 2000×2000 matrix), it will be necessary for head 22 to capture about 5000 area images 42, allowing for about 10% overlap between area images. If wafer 24 is to be scanned completely in one minute, light source 30 and sensor 36 should operate at 83 frames/sec. These requirements are cited only by way of example and may be adjusted depending on the actual size of wafer 24 and the actual resolution and throughput requirements of system 20.

Photodetector elements 37 in modern image sensors typically have a pitch of 4 µm. To achieve the desired resolution, objective 34 should thus have a magnification of approximately 2×. Image sensor 36 is typically a monochrome sensor, but it may alternatively comprise a color mosaic filter, as is known in the art, so as to form color area images of wafer 24 (albeit at reduced resolution). Alternatively, although only a single image sensor 36 is shown in FIG. 1, multiple sensors may be used, with suitable dichroic beam-splitters, so as to form color area images without loss of resolution.

In order to process all of area images 42, processor 38 must handle approximately 333 million pixels/sec. The operations performed by processor 38 may include rotation of the axes of area images 42 so that all the images are aligned within a common coordinate system. The pixels in the original area images are replaced by new, "virtual" pixels on the rotated axes. The intensity value of each new pixel is typically a weighted linear combination of a number of the values of the original pixels in its neighborhood, wherein the weighting coefficients are determined according to the known angular orientation of the original area image. As noted above, in order to perform this operation at the requisite speed, processor 38 preferably comprises special image-processing hardware, such as a programmable DSP or a suitable custom or semi-custom integrated circuit.

These elements of processor 38 may also be used to perform other image processing operations, particularly other neighborhood operations, such as edge enhancement and noise masking. Such operations typically involve convolution of the original pixel values in a given neighborhood with a suitable filter kernel, so as to determine enhanced output pixel values. The neighborhood used may extend over substantially any practical one- or two-dimensional domain. Image rotation, if required, may be carried out together with other image enhancement functions in a single two-dimensional computation.

After performing any desired image rotation and/or image enhancement operations on the area images, processor 38 analyzes the area images to find defects on wafer 24. Typical defects detected in this manner include contaminant particles, scratches and digs. Processor 38 then outputs data indicating the locations, types and other characteristics (such as size) of the defects it has discovered. Preferably, the defects are presented to a operator of system 20 in the form of a map, which can then be used by the operator in taking appropriate corrective action. Optionally, processor 38 stitches the area images together to form a composite image of the entire wafer. Where image features in adjacent area images are discernable, processor 38 preferably uses these features to register the area images precisely one with another. Values of pixels in areas of overlap between adjacent area images are typically averaged to provide a smooth transition from one area to the next.

Although preferred embodiments are described hereinabove with reference to inspection of semiconductor wafer 24, system 20 and the principles embodied therein may similarly be applied to inspection of substrates of other types, both in the microelectronics field and in other spheres. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for optical inspection of a surface of a substrate, the apparatus comprising: an optical head comprising a two-dimensional matrix of photodetectors, which is positioned opposite the substrate so as to capture a sequence of area images of respective areas of the surface; a rotation device, which is coupled to rotate the substrate about a rotation axis; a translation device, coupled to impart motion to at least one of the optical head and the rotation device so that the optical head is translated radially relative to the substrate while the rotation device rotates the substrate, whereby the area images in the sequence are arrayed in a spiral pattern with respect to the surface and each of the area images overlaps its neighboring ones of the area images in a direction along the spiral pattern; and an image processor, which is coupled to receive and process the area images so as to determine a characteristic of the surface.

2. Apparatus according to claim 1, and comprising a light source, which is adapted to emit pulsed illumination in synchronism with operation of the photodetectors so as to illuminate the respective areas of the surface.

3. Apparatus according to claim 2, wherein the pulsed illumination emitted by light source comprises incoherent radiation.

4. Apparatus according to claim 2, wherein the light source is angled relative to the optical head so that the area images are dark-field images.

5. Apparatus according to claim 1, wherein the optical head is operative to capture the sequence of area images while the rotation device rotates the substrate and while the optical head is translated radially relative to the substrate by the translation device.

6. Apparatus according to claim 1, wherein the area images comprise pixels, and wherein the image processor is adapted to apply a two-dimensional neighborhood operation to the pixels in the area images.

7. Apparatus according to claim 6, wherein the two-dimensional neighborhood operation comprises an image rotation operation.

8. Apparatus according to claim 1, wherein the image processor is adapted to process the area images so as to identify one or more defects on the surface.

9. Apparatus according to claim 8, wherein the substrate comprises a semiconductor wafer, and wherein the defects comprise at least one of a particle on the surface, a scratch in the surface and a dig in the surface.

10. Apparatus according to claim 1, wherein the processor is adapted to process the area images so as to form a combined image covering substantially all the respective areas.

11. A method for optical inspection of a surface of a substrate, the method comprising: scanning an optical head, which comprises a two-dimensional matrix of photodetectors, over the surface in a spiral pattern; capturing a sequence of two-dimensional area images of respective areas of the surface using the optical head while scanning the optical head over the surface in the spiral pattern such that each of the area images overlaps its neighboring ones of the area images in a direction along the spiral pattern; and processing the area images so as to determine a characteristic of the surface.

12. A method according to claim 11, wherein scanning the optical head comprises rotating the substrate about a rotation axis while imparting motion to at least one of the optical head and the substrate so that the optical head is translated over the surface in a radial direction relative to the rotation axis.

13. A method according to claim 11, wherein capturing the sequence of two-dimensional area images comprises illuminating the respective areas of the surface with pulsed illumination in synchronism with operation of the photodetectors.

14. A method according to claim 13, wherein illuminating the respective areas comprises illuminating the respective areas with incoherent radiation.

15. A method according to claim 13, wherein illuminating the respective areas comprises applying the illumination at an angle relative to the optical head so that the area images are dark-field images.

16. A method according to claim 11, wherein the area images comprise pixels, and wherein processing the area images comprises applying a two-dimensional neighborhood operation to the pixels in the area images.

17. A method according to claim 16, wherein applying the two-dimensional neighborhood operation comprises rotating the area images.

18. A method according to claim 11, wherein processing the area images comprises identifying one or more defects on the surface.

19. A method according to claim 18, wherein the substrate comprises a semiconductor wafer, and wherein identifying the one or more defects comprises finding at least one of a particle on the surface, a scratch in the surface and a dig in the surface.

20. A method according to claim 11, wherein processing the area images comprises combining the area images to form a combined image covering substantially all the respective areas.

* * * * *